(12) United States Patent
Emami (10) Patent No.: US 8,617,249 B2
(45) Date of Patent: Dec. 31, 2013

(54) GRAFT PROSTHETIC COMPOSITE FOR PROXIMAL HUMERUS

(75) Inventor: Ali Scott Emami, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 1476 days.

(21) Appl. No.: 11/242,305

(22) Filed: Oct. 3, 2005

(65) Prior Publication Data
US 2007/0078516 A1   Apr. 5, 2007

(51) Int. Cl.
*A61F 2/40* (2006.01)
(52) U.S. Cl.
USPC ........................................ 623/19.14
(58) Field of Classification Search
USPC ............... 623/19.11–19.14, 22.11–22.4, 623/23.11–23.46
See application file for complete search history.

(56) References Cited

U.S. PATENT DOCUMENTS

| 5,282,865 A | * | 2/1994 | Dong ..................... 623/19.14 |
| 5,725,592 A | * | 3/1998 | White et al. ............. 623/23.35 |
| 6,033,439 A | | 3/2000 | Camino et al. |
| 6,171,341 B1 | | 1/2001 | Boileau et al. |
| 6,334,874 B1 | | 1/2002 | Tornier et al. |
| 7,175,664 B1 | * | 2/2007 | Lakin ..................... 623/19.14 |

FOREIGN PATENT DOCUMENTS

| EP | 0821924 A1 | 2/1998 |
| EP | 1059071 A1 | 12/2000 |
| FR | 2726994 A1 | 5/1996 |
| WO | WO95/22302 A1 | 8/1995 |
| WO | WO2004/100838 A1 | 11/2004 |

OTHER PUBLICATIONS

Watson, *The Journal of Bone and Joint Surgery* 78-B:124-127 (Jan. 1996).
Kumar et al., *The Journal of Bone and Joint Surgery* 85-B:717-722 (Jul. 2003).
Ayoub et al., *The Journal of Bone and Joint Surgery* 81-B:495-500 (May 1999).
Malawer et al., *Surgery for Bone and Soft-Tissue Tumors*, Chapter 25, pp. 299-321 (1998).
Rödl et al., *The Journal of Bone and Joint Surgery* 84-B:1004-1008 (Sep. 2002).

(Continued)

*Primary Examiner* — David Isabella
*Assistant Examiner* — Ann Schillinger
(74) *Attorney, Agent, or Firm* — Schwegman, Lundberg & Woessner P.A.

(57) ABSTRACT

A proximal humeral prosthesis includes a humeral head having a distal end and a proximal end adapted to be coupled to a glenoid cavity of a scapula; a humeral stem core having an outer surface, a distal end, and a proximal end adapted to be coupled to the distal end of the humeral head; a humeral stem graft having an inner surface adapted to be coupled to at least a portion of the outer surface of the humeral stem core, a distal end, a proximal end, and an outer surface including at least one tendon attachment site; and an intramedullary stem having a proximal end adapted to be coupled to the distal end of the humeral stem core and a distal end adapted to be coupled to at least one bone of a skeleton. The prosthesis can be rendered modular and can further include a spacer segment. Resorption of bone from the humeral stem graft can be inhibited by compression of the humeral stem graft. Further, the prosthesis can include sites for attachment of soft tissues to the prosthesis, soft tissues for attachment to soft or bony tissues of the recipient, or both, which can improve function of the shoulder joint.

22 Claims, 8 Drawing Sheets

(56) References Cited

OTHER PUBLICATIONS

Henry et al., *Clinical Orthopaedics and Related Research* 396:231-239 (2002).
Kenan et al., *Skeletal Complications*, Chapter 145, pp. 2279-2290 (2002).
Padgett et al., "Oncologic Shoulder Arthrodesis: A Functional Assessment" (2002).
Biomet Inc., "Proximal Humeral Replacement™ System" (1996).
Shoulder Seminar, 2000 Specialty Day Program, Orlando, Florida (Mar. 18, 2000).
http://members.tripod.com/biothai/w9-3.html (date unknown).
International Search Report and Written Opinion issued in related PCT application No. PCT/US2006/035367.

* cited by examiner

GRAFT PROSTHETIC COMPOSITE FOR PROXIMAL HUMERUS

FIELD OF THE INVENTION

The present invention relates generally to the field of prosthetic replacement of resected portions of a mammalian skeleton, and more particularly, to a proximal humeral prosthesis.

BACKGROUND OF THE INVENTION

In a mammal, the humerus is the long bone of the upper portion of each anterior limb, for example, the human arm. As is commonly known in the art, the end of the humerus closest to the mammal's vertebral column is termed the proximal end and the end furthest from the mammal's vertebral column is termed the distal end. Further, the terms proximal and distal can be used to describe the relative orientation along the long axis of the humerus of any two points. For example, the anatomical neck of the native human humerus is proximal relative to the surgical neck of the native human humerus.

In *Homo sapiens*, the humeral head at the proximal end of the native humerus articulates with the glenoid cavity of the scapula to form the shoulder joint, and the extremity at the distal end articulates with the radius and ulna of the forearm to form the elbow.

A number of cancers can arise in the proximal portion of the humerus. Such cancers can include, but are not limited to, osteosarcoma, enchondroma, Ewing's sarcoma, periosteal chondroma, osteochondroma, chondroblastoma, chondromyxoid fibroma, aneurismal bone cyst, simple bone cyst, giant cell tumor of bone, chondrosarcoma, fibrous histiocytoma, fibrosarcoma of bone, and plasmacytoma, among others. Also, secondary tumors can form in the proximal portion of the humerus as a result of metastasis of primary tumors in other parts of the body. For example, about 15-20% of breast cancer patients develop humeral metastasis. Alternatively or in addition to chemotherapy or radiation, and if the tumor is not so advanced as to call for complete amputation of the limb, surgical resection of the tumorous region of the humerus can be performed as part of treatment. Surgical resection of the tumor frequently further involves resection of nearby soft tissues, such as the rotator cuff, the deltoid muscle, or at least one tendons or ligaments.

There are four main limb reconstruction options available after surgical resection of the proximal humerus: osteoarticular allograft reconstruction, allograft prosthetic composite, endoprosthetic replacement, and arthrodesis (the surgical fixation of a joint to promote bone fusion). The main goal of these reconstruction procedures is to stabilize the remainder of the upper extremity so the hand can be used in space. However, these procedures generally have poor functional results around the shoulder. These results are in most cases due to large amounts of soft tissues and soft tissue connection sites removed with the tumor to obtain a safe margin. The soft tissue resections can include the whole or part of the rotator cuff, the deltoid muscle, or other soft tissue structures and attachment points surrounding the proximal humerus. These resections limit the stability of the joint and the functional results.

Segmental endoprosthetics and allograft prosthetic composites are the most frequently used treatment options. Osteoarticular allografts are rarely used because of the risk of fracture of the humeral head. Arthrodesis is generally performed only if a resection removes a portion of the scapula containing the glenoid cavity.

All current treatment options are able to reconstruct the resected bone but in most cases there is an additional even larger need to address the soft tissues that stabilize the shoulder and provide active function. In most cases there is considerable loss or resection of soft tissue and soft tissue connection sites around the proximal humerus. Also, bone grafts in osteoarticular allografts or allograft prosthetic composites frequently suffer from resorption of bone. Therefore, a need exists for proximal humerus prostheses capable of imparting superior joint stability and functionality than those known in the art.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

In one embodiment, the present invention relates to a proximal humeral prosthesis including a humeral head having a distal end and a proximal end adapted to be coupled to a glenoid cavity of a scapula; a humeral stem core having an outer surface, a distal end, and a proximal end adapted to be coupled to the distal end of the humeral head; a humeral stem graft having an inner surface adapted to be coupled to at least a portion of the outer surface of the humeral stem core, a distal end, a proximal end, and an outer surface including at least one tendon attachment site; and an intramedullary stem having a proximal end adapted to be coupled to the distal end of the humeral stem core and a distal end adapted to be coupled to at least one bone of a skeleton.

In a further embodiment, the proximal humeral prosthesis further includes a spacer segment between the distal end of the humeral stem core and the proximal end of the intramedullary stem.

BRIEF DESCRIPTION OF THE DRAWINGS

The invention may be understood by reference to the following description taken in conjunction with the accompanying drawings, in which like reference numerals identify like elements, and in which.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would never-theless be a routine undertaking for those of ordinary skill in the art having the benefit of this disclosure.

The present invention will now be described with reference to the attached figures. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase. The word "or" is herein used in the inclusive sense unless explicitly specified to the contrary. Various anatomical reference terms used herein are intended to have the standard meaning for such terms as understood in the medical community. For example, the application may include reference to the following terms: anterior (the front, as opposed to the posterior); posterior (the back or behind, as opposed to the anterior); inferior (below, as opposed to superior); superior (above, as opposed to inferior); lateral (toward the left or right side of the body, as opposed to medial); medial (in the middle or inside, as opposed to lateral); proximal (toward the beginning, as opposed to distal); and distal (further from the beginning, as opposed to proximal).

Figure 1A:
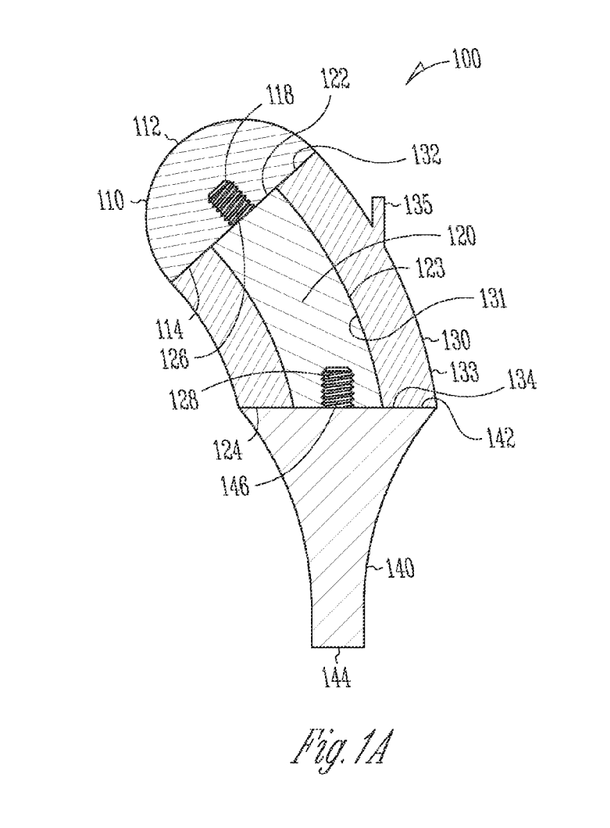
FIGS. 1A and 1B each show a cross-sectional side view of a proximal humeral prosthesis.
Figure 1B:
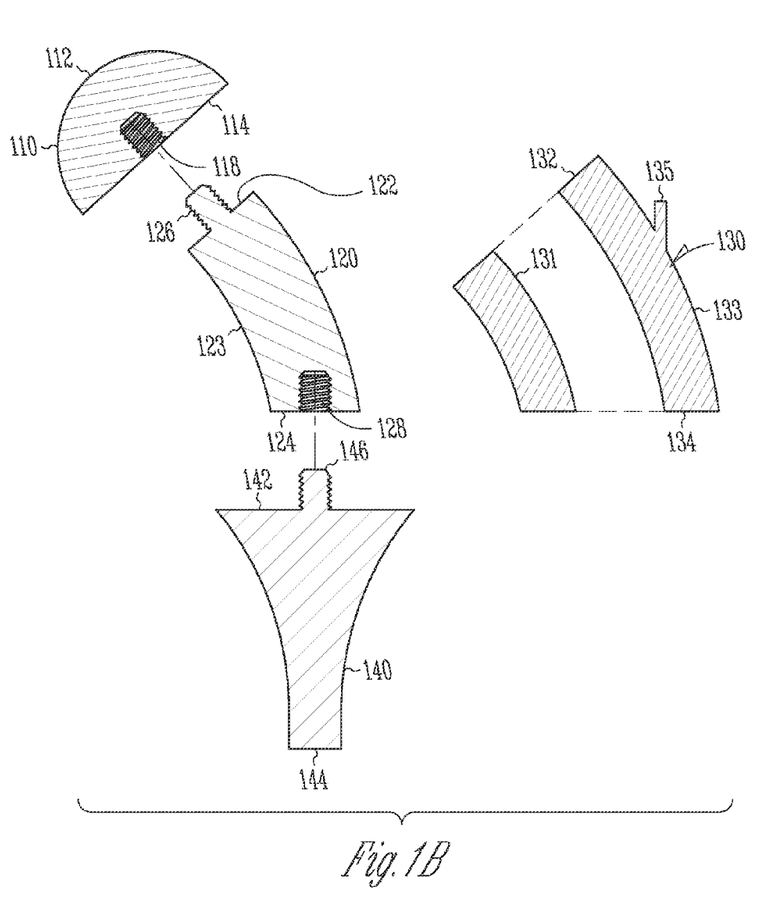

FIGS. 1A-1B are, respectively, a cross-sectional view of an assembled proximal humeral prosthesis 100 and an exploded view of the proximal humeral prosthesis 100. As shown in FIGS. 1A-1B, the proximal humeral prosthesis 100 includes a humeral head 110 having a proximal end 112 and a distal end 114; a humeral stem core 120 having a proximal end 122, a distal end 124, and an outer surface 123; a humeral stem graft 130 having a proximal end 132, a distal end 134, an inner surface 131, an outer surface 133, and at least one tendon attachment site 135 on the outer surface 133; and an intramedullary stem 140 having a proximal end 142 and a distal end 144.

The humeral head 110, humeral stem core 120, and intramedullary stem 140 can be formed of any suitable non-bone material, such as a metal (including, but not limited to, cobalt, chromium, titanium, and alloys including at least one thereof, among others), a ceramic, cement, or a plastic, among others known to the skilled artisan. The humeral stem graft 130 can be formed of any suitable bone or portion thereof. A graft is a portion of tissue, such as bone, taken from an animal. "Graft" is used herein to encompass a homograft (a portion of tissue, such as bone, taken from the same individual that will receive the prosthesis), an allograft (a portion of tissue, such as bone, taken from a donor of the same species as the recipient), and a xenograft (a portion of tissue, such as bone, taken from a donor of a different species than the recipient). The graft can be taken directly from the donor or it can be modified after removal from the donor by changing the size or shape to improve its fit in its intended destination or for other reasons.

The humeral stem graft 130 includes at least one tendon attachment site 135 on its outer surface 133. The tendon attachment site 135 can allow attachment of at least one tendon, at least one muscle, and/or at least one ligament from the recipient's native soft tissues to the proximal humeral prosthesis 100. The term "tendon attachment site" is used for convenience and is not to be construed as limiting the invention to the attachment of at least one tendon from the recipient's native soft tissues. Each tendon attachment site 135 can be independently a hole, a loop, a threaded member, a tack, or a tendon or portion of a tendon attached to the graft 130 in its native state (prior to donation) and retained during processing of the native bone into graft form. In one embodiment, each tendon attachment site 135 is a tendon or a portion of a tendon retained on the graft 130 after processing. This tendon or portion of tendon retained on the graft 130 after donation can be readily attached (for example, by sutures) to at least one tendon, at least one muscle, and/or at least one ligament from the recipient's soft tissues during implantation of the proximal humeral prosthesis 100. The graft 130 may include multiple tendon attachment sites 135.

Figure 7A:
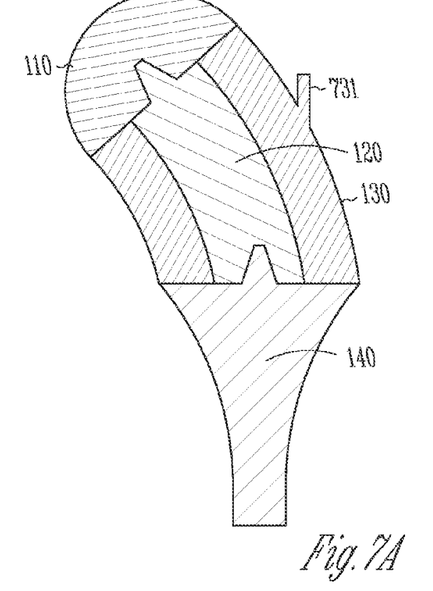
FIGS. 7A-7E show cross-sectional side views of a proximal humeral prosthesis containing various tendon attachment sites.

Other embodiments of the tendon attachment site are shown in FIGS. 7A-7E. In one embodiment, each tendon attachment site 135 can be a loop formed from a fabric (such as Dacron), a polymer, or a metal (such as cobalt, chromium, or titanium), or a loop fabricated as an integral component of the part of the humeral stem graft 130. FIG. 7A shows the latter embodiment in cross-section, wherein a loop 731 is defined by drilling or other appropriate processing of the humeral stem graft 130. FIG. 7A shows one loop 731, but one, two, three, four, or more loops 731 can be employed.

Figure 7B:
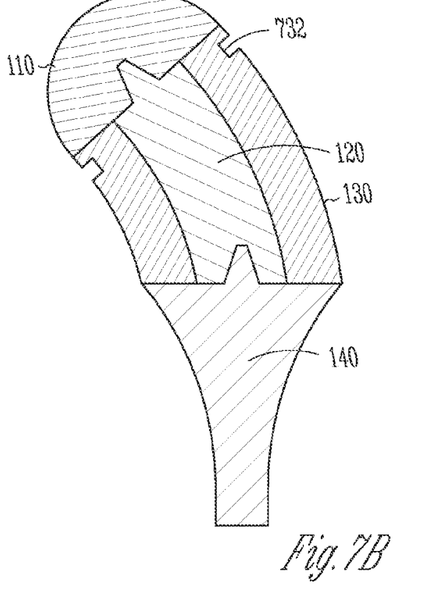

In another embodiment, each tendon attachment site 135 can be a locking ring that it is capable of seating at or around the humeral stem graft 130. As shown in FIG. 7B, the humeral stem graft 130 can be fabricated to have a retaining groove 732 within which a locking ring (not shown) can be partially or wholly seated. In one embodiment, the locking ring can be provided in a first unlocked state and at least one soft tissues of the recipient can be placed between the locking ring and the proximal humeral prosthesis, at which time the locking ring can be changed to a second locked state capable of capturing the soft tissues between the locking ring and the proximal humeral prosthesis.

Figure 7C:
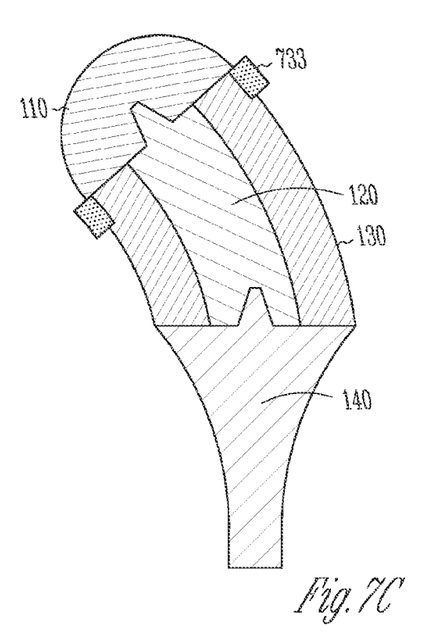

In another embodiment, as shown in FIG. 7C, each tendon attachment site 135 can be a sewing cuff 733 formed from a fabric such as Dacron, among others, that is capable of seating at or around a portion of the humeral stem graft 130. At least one soft tissue of the recipient can be sutured to the sewing cuff 733 by techniques known in the art.

Figure 7D:
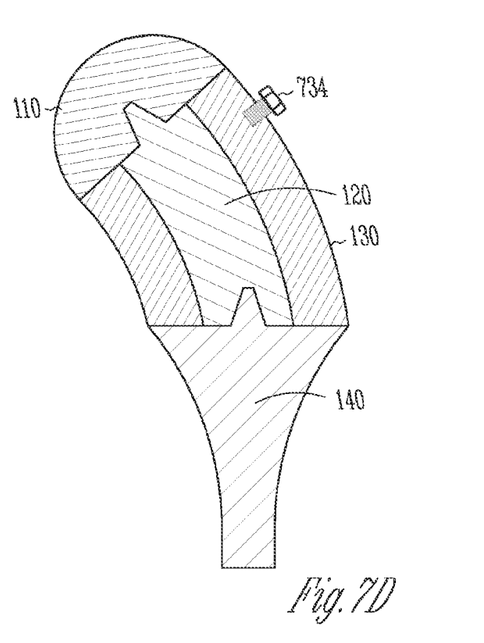

In another embodiment, as shown in FIG. 7D, each tendon attachment site 135 can be a threaded member 734 formed from any appropriate material, such as a metal, and threaded into a portion of the humeral stem graft 130. The threaded member 734 can have a threaded taper and a head. Depending on the material and structure of the threaded member and the material and structure of the humeral stem graft 130, among other parameters, the humeral stem graft 130 can be pre-drilled with a threaded bore or an unthreaded bore or the threaded member 734 can be self-drilling. At least one soft tissue of the recipient can be sutured or otherwise affixed by known means to the head of the threaded member 734. FIG.

7D shows one threaded member 734, but one, two, three, four, or more threaded members 734 can be employed.

Figure 7E:
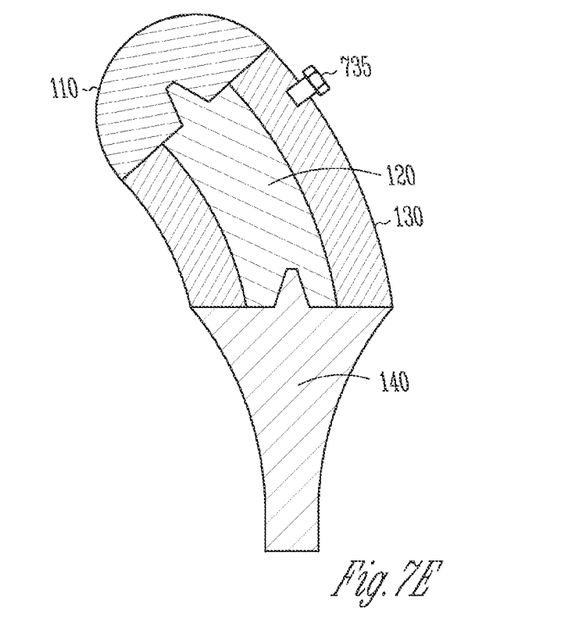

In another embodiment, as shown in FIG. 7E, each tendon attachment site 135 can be a tack 735 formed from any appropriate material, such as a metal, and driven by pressure into the humeral stem graft 130. The tack 735 can have a taper and a head. At least one soft tissue of the recipient can be sutured or otherwise affixed by known means to the head of the tack 735. FIG. 7E shows one tack 735, but one, two, three, four, or more tacks 735 can be employed.

The humeral stem graft 130 can be completely positioned around the humeral stem core 120 (i.e., the outer surface 123 of the humeral stem core 120 can be fully concealed by the humeral stem graft 130), or it can be incompletely positioned around the humeral stem core 120 (i.e., at least a portion of the outer surface 123 can be exposed). The humeral stem graft 130 shown in FIGS. 1A-1B has a single tendon attachment site 135, but multiple tendon attachment sites 135 are possible though not shown.

In one embodiment, the humeral head 110 is adapted to be coupled to the humeral stem core 120 and the humeral stem core 120 is adapted to be coupled to the intramedullary stem 140, as will be described more fully below.

Figure 2A:
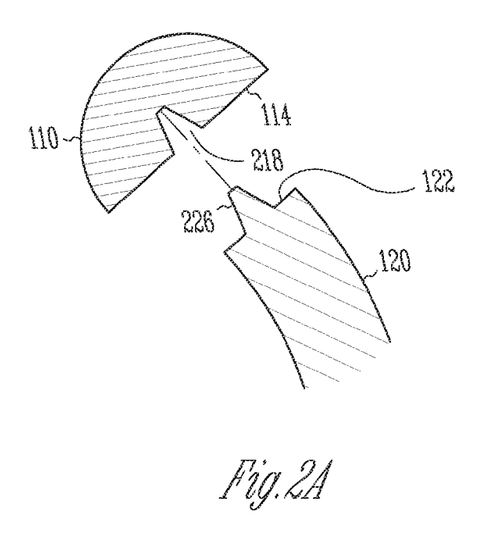
FIGS. 2A, 2B, and 2C each show a cross-sectional side view of particular embodiments of attachment of components of the proximal humeral prosthesis to one another.

The distal end 112 of the humeral head 110 is adapted to be coupled to the glenoid cavity of a mammalian scapula, and as such typically has a hemispherical or approximately hemispherical shape. The humeral head 110 can be attached to the humeral stem core 120 by any of a variety of known techniques. FIGS. 1A-1B and 2A show two illustrative embodiments for this attachment. In FIG. 1, the distal end 114 of the humeral head 110 includes a threaded bore 118 capable of engaging by threading with a threaded member 126 extending from the proximal end 122 of the humeral stem core 120. The threaded member 126 can be formed integrally with the humeral stem core 120 or it can be formed separately and attached to the humeral stem core 120 by any appropriate technique. Alternate arrangements of the threaded bore 118 and the threaded member 126 and the number of threaded bores 118 and threaded members 126 may also be employed, if desired, or cement or an adhesive can be used to promote attachment.

In FIG. 2A, the distal end 114 of the humeral head 110 includes a bore 218 capable of engaging a taper 226 extending from the proximal end 122 of the humeral stem core 120. The taper 226 can be formed integrally with the humeral stem core 120 or it can be formed separately and attached to the humeral stem core 120 by any appropriate technique. The skilled artisan will understand an alternative arrangement of the bore 218 and the taper 226, wherein the bore 218 is a component of the proximal end 122 of the humeral stem core 120 and the taper 226 extends from the distal end 114 of the humeral head 110, although this alternative is not shown. Multiple bores 218 and tapers 226 may also be employed, if desired. Engagement between the bore 218 and the taper 226 can be encouraged by the use of cement or an adhesive.

Figure 2B:
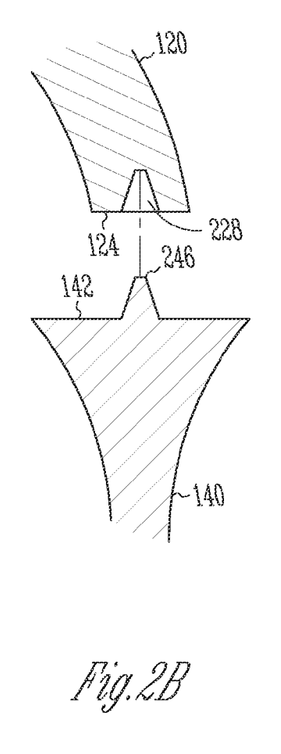

The humeral stem core 120 can be attached to the intramedullary stem 140 by any of a variety of known techniques. The humeral stem core 120 can be directly coupled to the intramedullary stem 140 or it can be indirectly coupled to the intramedullary stem 140 (i.e., coupled to an intervening spacer). FIGS. 1A-1B and 2B show two illustrative embodiments for direct coupling of the humeral stem core 120 and the intramedullary stem 140. In FIG. 1, the distal end 124 of the humeral stem core 120 includes a threaded bore 128 capable of engaging by threading with a threaded member 146 extending from the proximal end 142 of the intramedullary stem 140. The threaded member 146 can be formed integrally with the intramedullary stem 140 or it can be formed separately and attached to the intramedullary stem 140 by any appropriate technique. Alternate arrangements of the threaded bore 128 and the threaded member 146 and the number of threaded bores 128 and threaded members 146 may also be employed, if desired, or cement or an adhesive can be used to promote attachment.

In FIG. 2B, the distal end 124 of the humeral stem core 120 includes a bore 228 capable of engaging a taper 246 extending from the proximal end 142 of the intramedullary stem 140. The taper 246 can be formed integrally with the intramedullary stem 140 or it can be formed separately and attached to the intramedullary stem 140 by any appropriate technique. The skilled artisan will understand an alternative arrangement of the bore 228 and the taper 246, wherein the bore 228 is a component of the proximal end 142 of the intramedullary stem 140 and the taper 246 extends from the distal end 124 of the humeral stem core 120, although this alternative is not shown. Multiple bores 228 and tapers 246 may also be employed, if desired. Engagement between the bore 228 and the taper 246 can be encouraged by the use of cement or an adhesive.

The humeral head 110 and the humeral stem core 120 can be formed as an integral unit, if desired, in which case the formation as an integral unit is an adaptation for coupling of the humeral head 110 and the humeral stem core 120. Similarly, the humeral stem core 120 and the intramedullary stem 140 can be formed as an integral unit. In another embodiment, the humeral head 110, the humeral stem core 120, and the intramedullary stem 140 can be formed as an integral unit. If any two adjacent components are not formed as an integral unit, they can be attached to one another by any of the techniques discussed above.

Any two adjacent components of the proximal humeral prosthesis 100 can be coupled by the use of a structural feature of another component of the proximal humeral prosthesis 100. For example, FIG. 8B shows an embodiment wherein humeral stem core 120 includes a bore therethrough which is adapted to seat a taper 146 of the intramedullary stem 140 and the humeral head 110 includes a bore 118 which is adapted to seat the taper. The humeral head 110 and the humeral stem core 120 can be coupled by engagement of the taper 146 in the bores thereof. The use of a threaded member instead of the taper 146 or other modifications are a routine matter for the skilled artisan having the benefit of the present disclosure.

The humeral stem graft 130 can be positioned around the humeral stem core 120 by any appropriate technique. In one embodiment, the positioning may involve no contact between the two, if the humeral stem graft 130 can be retained in place by contact with the distal end 114 of the humeral head 110 and the proximal end 142 of the intramedullary stem 140, as will be described below in more detail. In another embodiment, positioning may include contact, i.e., the humeral stem core 120 can be inserted into the humeral stem graft 130 in such a way that friction between the outer surface 123 of the humeral stem core 120 and the inner surface 131 of the humeral stem graft 130 retains the humeral stem graft 130 in position relative to the humeral stem core 120. In another embodiment, the positioning may include contact encouraged by the use of cement or an adhesive. In any of the foregoing embodiment, the humeral stem graft 130 can be provided as one piece or multiple pieces that can each be independently positioned, contacted, or cemented or adhered into place.

Regardless of the positioning technique between the humeral stem graft 130 and the humeral stem core 120, in one embodiment, the proximal end 132 of the humeral stem graft 130 can be adapted to contact the distal end 114 of the humeral head 110, the distal end 134 of the humeral stem graft 130 can be adapted to contact the proximal end 142 of the intramedullary stem 140, and the humeral head 110 can be attached to the humeral stem core 120 and the intramedullary stem 140 can be attached to the humeral stem core 120 in such a manner that a compressive force can arise from the humeral head 110 or the intramedullary stem 140 and be exerted axially on the humeral stem graft 130. In an embodiment wherein the humeral head 110 and the humeral stem core 120 or the humeral stem core 120 and the intramedullary stem 140 are threadably connected, a compressive force can be generated by tightening the threaded connection to a desired extent. Exerting a compressive force on the humeral stem graft 130 may minimize resorption of bone from the humeral stem graft 130.

Figure 2C:
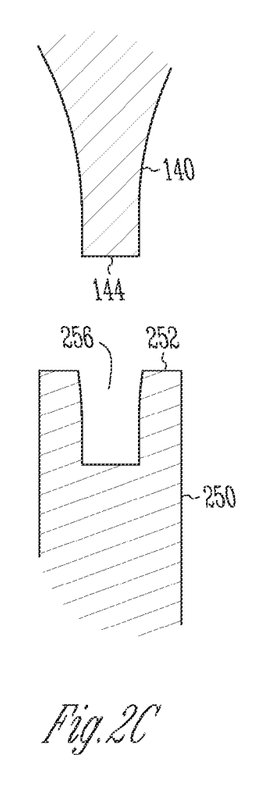

The proximal humeral prosthesis 100 can be implanted to replace a resected humerus or proximal portion of a humerus of a mammal. The proximal end 112 of the humeral head 110 can be coupled to the glenoid cavity of the mammal's scapula (not shown). The scapula can be native bone, a bone graft, a synthetic material, or a combination of two or more thereof, and the glenoid cavity can be native to the scapula or generated by processing of the material to form the scapula. The distal end 144 of the intramedullary stem 140 can be coupled to at least one bone of the skeleton. The bone can be native bone, a bone graft, a synthetic material, or a combination of two or more thereof. In one embodiment, shown in exploded view in FIG. 2C, the distal end 144 can be coupled to the proximal surface 252 of a non-resected distal portion 250 of a native humerus. The distal portion 250 can be prepared by drilling a bore 256 adapted to couple the proximal end 144 of the intramedullary stem 140 in the proximal surface 252 of the distal portion 250. The coupling can be encouraged by the use of cement or an adhesive.

Figure 3A:
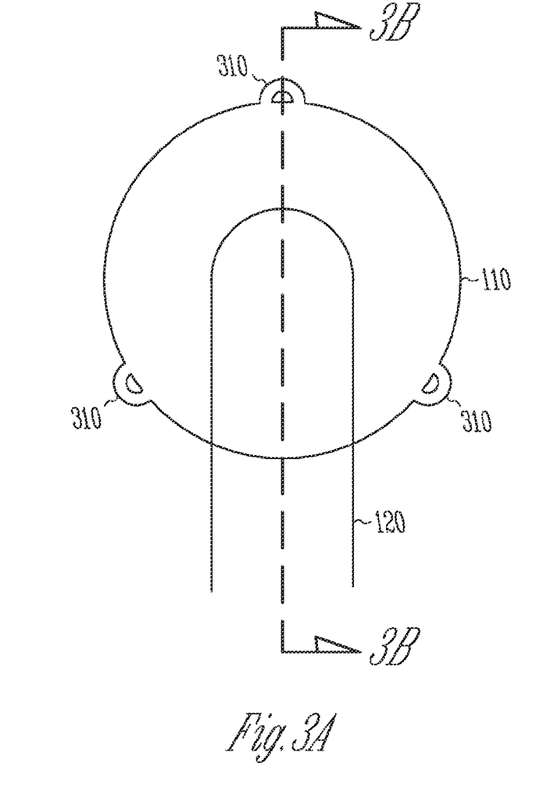
FIG. 3A shows an end view and FIG. 3B shows a cross-sectional side view of a humeral head and a humeral stem core.
Figure 3B:
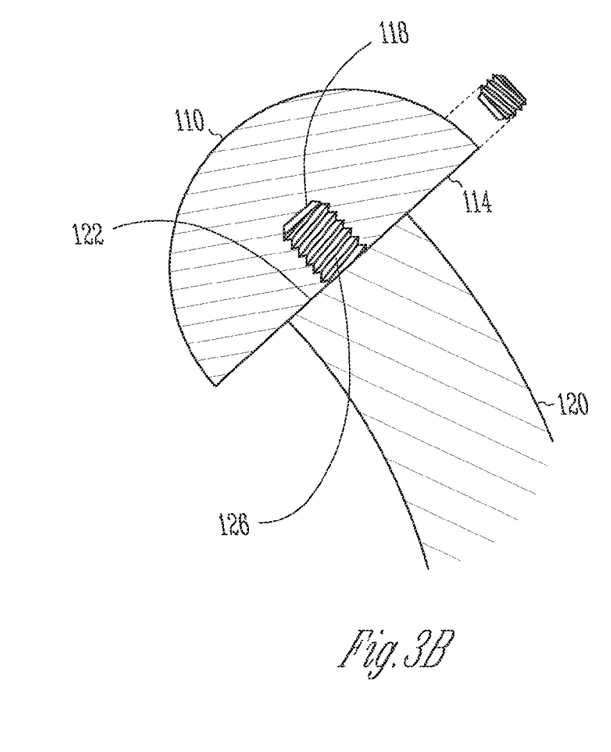

The proximal humeral prosthesis 100 can include at least one soft tissue connection site. The soft tissue connection site is formed on or attached to a non-bone portion of the proximal humeral prosthesis 100 and the soft tissue connection site does not include a tendon or portion of a tendon. Each soft tissue connection site may be of any desired shape or size and may be made from a variety of materials. Exemplary soft tissue connection sites include, but are not limited to, loops, locking rings, sewing cuffs, threaded members, or tacks, among others. General descriptions of these soft tissue connection sites have been given above. Moreover, each soft tissue connection site may be formed integrally with a component of the proximal humeral prosthesis 100 or may be formed as a separate component that can be attached to the component. Turning to FIGS. 3A-3B, FIG. 3A is an end view of a humeral head 110 and a humeral stem core 120 and FIG. 3B shows a cross-sectional side view of the humeral head 110 and the humeral stem core 120. (In the interest of clarity, the humeral stem graft 130 is not shown). As shown in this embodiment, the humeral head 110 includes a plurality of soft tissue connection sites in the form of loops 310 located around the periphery of the distal end 114 of the humeral head 110. Three loops 310 are shown in FIG. 3A, but one, two, three, four, or more loops 310 or other soft tissue connection sites may be employed depending on the intended application of the proximal humeral prosthesis 100.

In addition to the components listed above, in one embodiment the proximal humeral prosthesis 100 can further include at least one tendon, muscle, ligament, cartilaginous structure, or other non-bony tissue coupled to at least one tendon attachment site 135 of the humeral stem graft 130, wherein such tendon, muscle, ligament, cartilaginous structure, or other non-bony tissue is a graft. In one embodiment, the tendon, muscle, or ligament can be provided from the same site in the same donor as the bone formed into the humeral stem graft 130, or it can be provided from a different site in the same donor or from the homologous site or a different site in a different donor and attached to the tendon attachment site during processing of components to form the proximal humeral prosthesis 100. Such a tendon, muscle, or ligament can further stabilize or impart functionality to the proximal humeral prosthesis 100 after implantation by allowing the surgeon to attach the tendon, muscle, or ligament of the proximal humeral prosthesis 100 to native soft tissues of the recipient.

Figure 6:
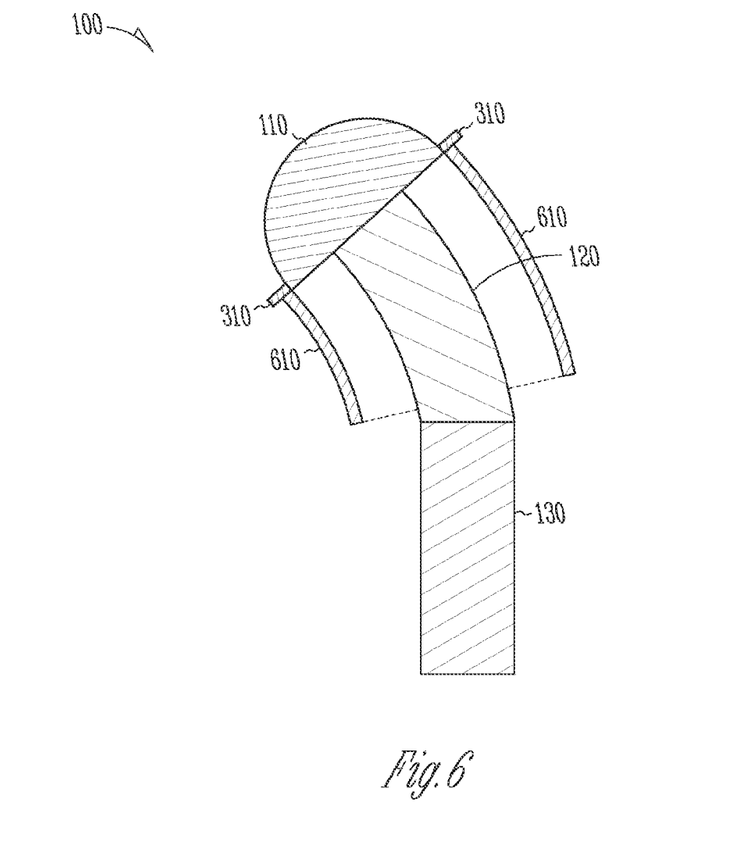
FIG. 6 shows a schematic cross-sectional side view of a proximal humeral prosthesis including a synthetic vascular graft.

In another embodiment, the proximal humeral prosthesis 100 can further include a synthetic soft tissue, such as a synthetic vascular graft or a cross-linked biological tissue. FIG. 6 shows a proximal humeral prosthesis 100 according to this embodiment. The synthetic vascular graft 610 can be made from a fabric such as Dacron or a processed biological tissue such as cross-linked bovine pericardium, among others. In FIG. 6, the synthetic vascular graft 610 is shown as attached to the remainder of the prosthesis 100 by suturing to soft tissue attachment loops 310. The loops 310 can be used for attachment of both recipient soft tissues and soft tissues included with the prosthesis 100.

Figure 4:
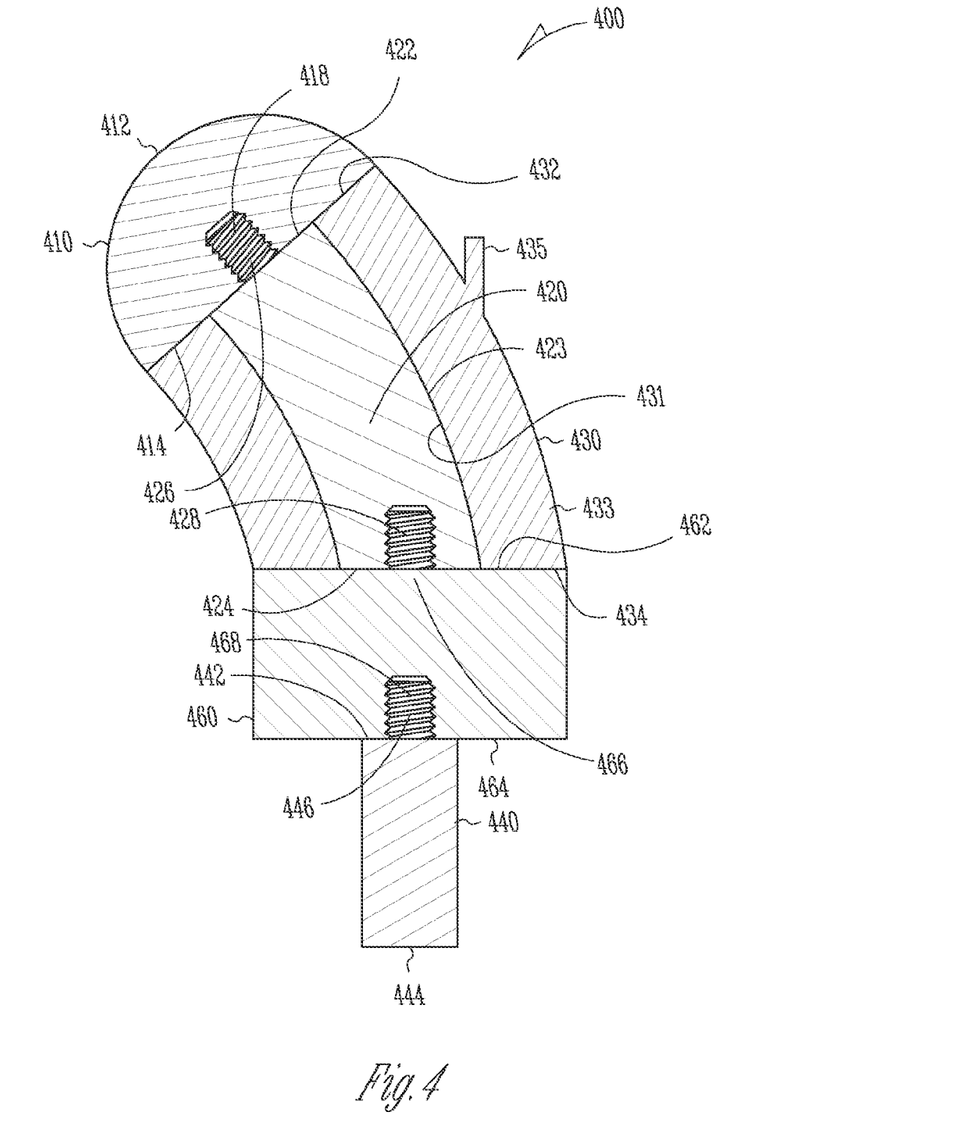
FIG. 4 shows a cross-sectional side view of a proximal humeral prosthesis.

Turning to FIG. 4, in another embodiment, the proximal humeral prosthesis 400 further includes a spacer segment 460 situated between the humeral stem core 420 and the intramedullary stem 440 (i.e., the humeral stem core 420 and the intramedullary stem 440 are indirectly coupled). FIG. 4 shows a single spacer segment 460, but multiple spacer segments 460 are possible. The use of a spacer segment 460 increases the modularity and ease of implantation of the prosthesis 400 by allowing the surgeon to readily change the length of the prosthesis to fit the resected portion of the humerus by inserting a spacer segment 460 of a desired length into the prosthesis 400. The spacer segment 460 can be made from any suitable non-bone material. The spacer segment 460 can be attached to the prosthesis 400 in a manner to impart a compressive force on the humeral stem graft 430.

Figure 5A:
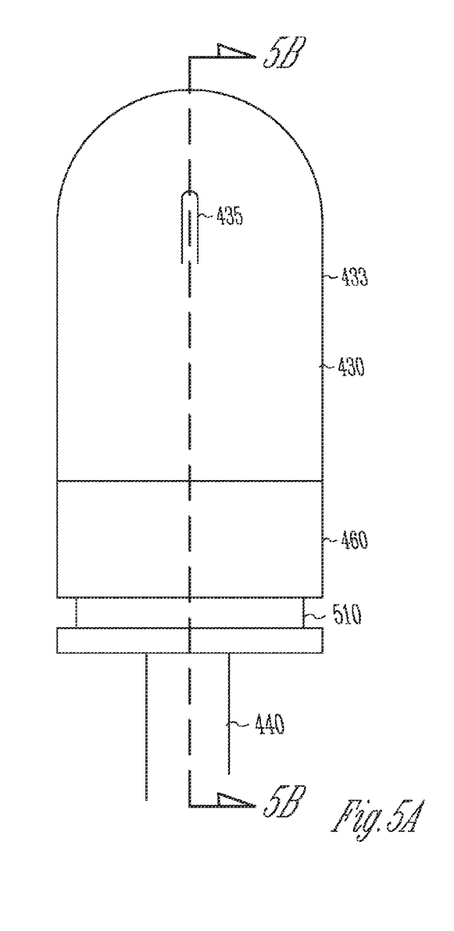
FIG. 5A shows an end view and FIG. 5B shows a cross-sectional side view of a proximal humeral prosthesis.
Figure 5B:
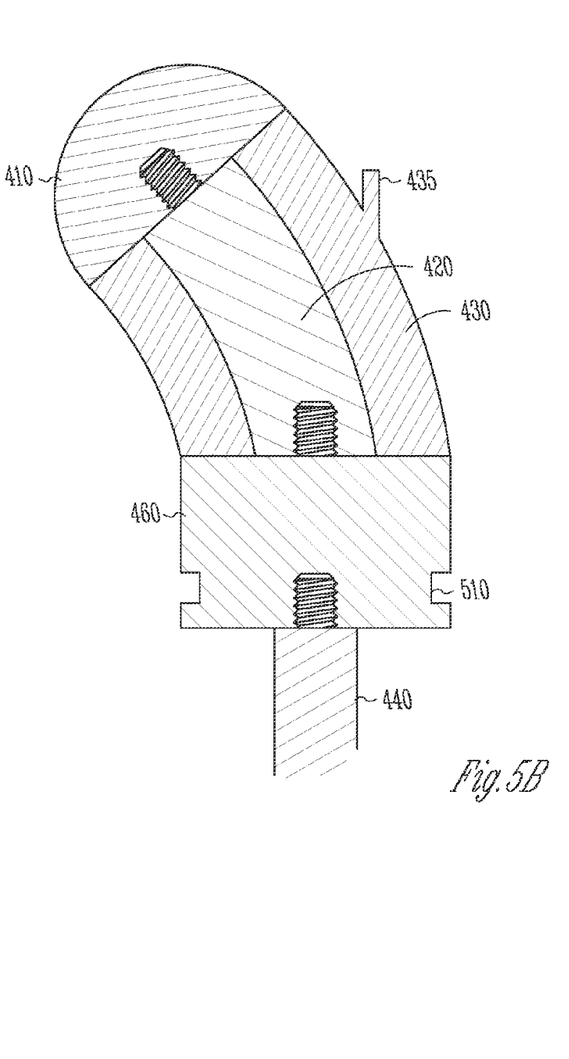

The spacer segment 460 can include at least one soft tissue connection site 510. In FIG. 5A, a portion of a prosthesis is shown in end view, wherein the spacer segment 460 includes a groove 510 located around the periphery of the spacer segment 460. The groove 510 is suitable for seating a locking ring (not shown) suitable for use as a soft tissue connection site. FIG. 5B shows the same prosthesis portion in a cross-sectional side view.

Figure 8A:
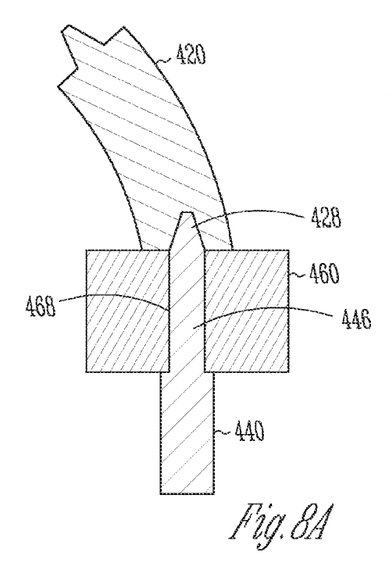
FIGS. 8A-8B show cross-sectional side views of particular couplings of components of proximal humeral prostheses.
Figure 8B:
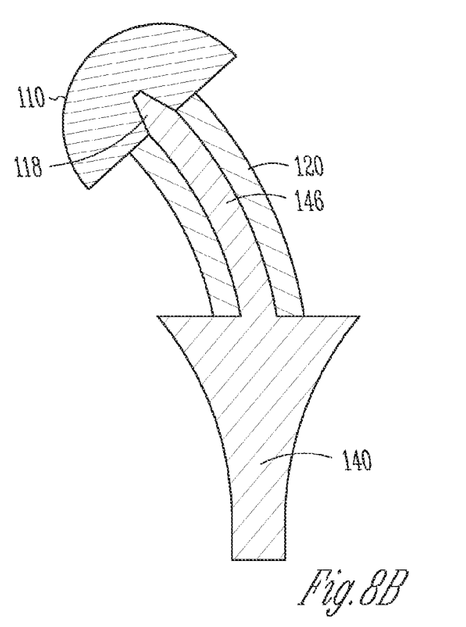

FIG. 8A shows an embodiment wherein the spacer segment 460 includes a bore 468 therethrough which is adapted to seat a taper 446 of the intramedullary stem 440 and the humeral stem core 420 includes a bore 428 which is adapted to seat the taper 446. The humeral stem core 420 and the spacer segment 460 can be coupled by engagement of the taper 446 in the bores 428 and 468. The use of a threaded member instead of the taper 446 or other modifications are a routine matter for the skilled artisan having the benefit of the present disclosure.

In one embodiment, a collection of humeral heads of differing sizes and configurations, a collection of humeral stem cores of differing sizes and configurations, and a collection of intramedullary stems of differing sizes and configurations can be provided. In this embodiment, the surgeon can readily assemble the complete proximal humeral prosthesis in light of the specifics of the structures of the scapula and humerus, mixing and matching each part so as to provide optimal fit of each part to each other part and of each part to the whole of the skeletal system.

All of the apparatus and methods disclosed and claimed herein can be made and executed without undue experimentation in light of the present disclosure. While the apparatus and methods of this invention have been described in terms of particular embodiments, it will be apparent to those of skill in the art that variations may be applied to the apparatus and methods and in the steps or in the sequence of steps of the methods described herein without departing from the concept, spirit and scope of the invention as defined by the appended claims.

What is claimed is:

1. A proximal humeral prosthesis, comprising:
   a humeral head having a distal end and a proximal end, said proximal end of said humeral head adapted to be coupled to a glenoid cavity of a scapula;
   a humeral stem core having an outer surface, a distal end, and a proximal end, said proximal end of said humeral stem core adapted to be coupled to the distal end of the humeral head;
   a humeral stem graft having an inner surface, a distal end, a proximal end, and an outer surface comprising at least one tendon attachment site, said inner surface of said humeral stem graft adapted to be positioned around at least a portion of the outer surface of the humeral stem core with said proximal end of said humeral stem graft contacting the distal end of the humeral head to axially compress said humeral stem graft beneath the humeral head being axially compressed; and
   an intramedullary stem having a proximal end and a distal end, said proximal end of said intramedullary stem adapted to be directly coupled or indirectly coupled to the distal end of the humeral stem core.

2. The proximal humeral prosthesis of claim 1, wherein the proximal end of the humeral stem graft is adapted to contact the distal end of the humeral head, the distal end of the humeral stem graft is adapted to contact the proximal end of the intramedullary stem, and the humeral stem graft is compressed between the humeral head and the intramedullary stem.

3. The proximal humeral prosthesis of claim 1, wherein the humeral head is coupled to the humeral stem core by at least one of cement, at least one taper, or at least one threaded member.

4. The proximal humeral prosthesis of claim 1, wherein the humeral stem core is coupled to the intramedullary stem by at least one of cement, at least one taper, or at least one threaded member.

5. The proximal humeral prosthesis of claim 1, wherein the humeral stem graft is adapted to be coupled to at least said portion of said outer surface of said humeral stem core.

6. The proximal humeral prosthesis of claim 5, wherein the humeral stem graft is coupled to the humeral stem core by cement.

7. The proximal humeral prosthesis of claim 1, wherein the humeral stem graft fully surrounds the outer surface of said humeral stem core.

8. The proximal humeral prosthesis of claim 1, wherein the humeral head further comprises at least one soft tissue connection site.

9. The proximal humeral prosthesis of claim 8, wherein each soft tissue connection site is independently a loop, a locking ring, a sewing cuff, a threaded member, or a tack.

10. The proximal humeral prosthesis of claim 1, further comprising a spacer segment having a distal end and a proximal end, said proximal end of said spacer segment adapted to be coupled to the distal end of the humeral stem core and said proximal end of said intramedullary stem adapted to be coupled to the distal end of said spacer segment.

11. The proximal humeral prosthesis of claim 10, wherein the humeral stem graft is axially compressed between the humeral head and the spacer segment.

12. The proximal humeral prosthesis of claim 1, wherein the inner surface of the humeral stem graft is positioned around the humeral stem core with the distal end of the humeral stem graft contacting an adjacent component, the adjacent component including one of a spacer segment and the intramedullary stem, to axially compress the humeral stem graft between the humeral head and the adjacent component.

13. A proximal humeral prosthesis, comprising:
    a humeral head having a distal end and a proximal end, said proximal end of said humeral head adapted to be coupled to a glenoid cavity of a scapula;
    a humeral stem core having an outer surface, a distal end, and a proximal end, said proximal end of said humeral stem core adapted to be coupled to the distal end of the humeral head;
    a humeral stem graft having an inner surface, a distal end, a proximal end, and an outer surface comprising at least one tendon attachment site, said inner surface of said humeral stem graft adapted to be positioned around at least a portion of the outer surface of the humeral stem core with said proximal end of said humeral stem graft contacting the distal end of the humeral head and said distal end of said humeral stem graft contacting the proximal end of the spacer segment to axially compress said humeral stem graft between the humeral head and the spacer segment being axially compressed;
    a spacer segment having a distal end and a proximal end, said proximal end of said spacer segment adapted to be coupled to the distal end of the humeral stem core; and
    an intramedullary stem having a proximal end and a distal end, said proximal end of said intramedullary stem adapted to be coupled to the distal end of the spacer segment.

14. The proximal humeral prosthesis of claim 13, wherein the humeral head is coupled to the humeral stem core by at least one of cement, at least one taper, or at least one threaded member.

15. The proximal humeral prosthesis of claim 13, wherein the humeral stem core is coupled to the spacer segment by at least one of cement, at least one taper, or at least one threaded member.

16. The proximal humeral prosthesis of claim 13, wherein the humeral stem graft is adapted to be coupled to at least said portion of said outer surface of said humeral stem core.

17. The proximal humeral prosthesis of claim 16, wherein the humeral stem graft is coupled to the humeral stem core by cement.

18. The proximal humeral prosthesis of claim 13, wherein the humeral stem graft fully surrounds the outer surface of said humeral stem core.

19. The proximal humeral prosthesis of claim 13, wherein the humeral head further comprises at least one soft tissue connection site.

20. The proximal humeral prosthesis of claim 19, wherein each soft tissue connection site is independently a loop, a locking ring, a sewing cuff, a threaded member, or a tack.

21. The proximal humeral prosthesis of claim 13, wherein the spacer segment further comprises at least one soft tissue connection site.

22. The proximal humeral prosthesis of claim 21, wherein each soft tissue connection site is independently a loop, a locking ring, a sewing cuff, a threaded member, or a tack.

* * * * *